US007682369B2

(12) United States Patent
Séguin

(10) Patent No.: US 7,682,369 B2
(45) **Date of Patent: *Mar. 23, 2010**

(54) SURGICAL DEVICE FOR CONNECTING SOFT TISSUE

(75) Inventor: Jacques Séguin, Paris (FR)

(73) Assignee: Evalve, Inc., Menlo Park, CA (US)

( * ) Notice: Subject to any disclaimer, the term of this patent is extended or adjusted under 35 U.S.C. 154(b) by 1074 days.

This patent is subject to a terminal disclaimer.

(21) Appl. No.: 11/354,612

(22) Filed: Feb. 14, 2006

(65) Prior Publication Data

US 2006/0135993 A1 Jun. 22, 2006

Related U.S. Application Data

(60) Continuation of application No. 10/877,279, filed on Jun. 24, 2004, now Pat. No. 7,288,097, which is a division of application No. 10/202,599, filed on Jul. 24, 2002, now Pat. No. 6,770,083, which is a division of application No. 09/523,018, filed on Mar. 10, 2000, now Pat. No. 6,461,366, which is a continuation of application No. PCT/FR98/01960, filed on Sep. 12, 1997.

(51) Int. Cl.
*A61B 17/00* (2006.01)

(52) U.S. Cl. ...................................................... 606/142

(58) Field of Classification Search ................. 606/139, 606/142–144, 151, 157, 148, 185, 42

See application file for complete search history.

(56) References Cited

U.S. PATENT DOCUMENTS 2,108,206 A 2/1938 Meeker
3,378,010 A 4/1968 Codling et al.
3,761,979 A 10/1973 Moulopoulos
3,874,338 A 4/1975 Happel (Continued)

FOREIGN PATENT DOCUMENTS

DE 3504292 7/1986

(Continued)

OTHER PUBLICATIONS

Abe et al., "De Vega's Annuloplasty for Acquired Tricuspid Disease: Early and Late Results in 110 Patients" *Ann. Thorac. Surg.* (1989) 48:670-676.

(Continued)

*Primary Examiner*—Kevin T Truong
(74) *Attorney, Agent, or Firm*—Townsend and Townsend and Crew LLP; Jonathan Feuchtwang, Esq.

(57) ABSTRACT

The invention comprises a surgical instrument including an external tube (2) and two elongated members (4) positioned in said tube (2), each of which includes a distal end (10*a*) for capturing one of the two tissue zones (M1, M2) to be attached. The instrument (1) may further comprise a catching member (22, 25) for each tissue (M1, M2) to be attached; a rod (15, 16) linked to each catching member (22, 25) enabling tension to move axially, said rod (15, 16) being separable from said catching member (22, 25) when a tension is exerted on it beyond a certain threshold; and a member (17*a*) forming a stop for locking axially each catching member (22, 25) during said tension.

10 Claims, 4 Drawing Sheets

U.S. PATENT DOCUMENTS

| | | | | |
|---|---|---|---|---|
| 4,056,854 | A | 11/1977 | Boretos et al. | |
| 4,297,749 | A | 11/1981 | Davis et al. | |
| 4,484,579 | A | 11/1984 | Meno et al. | |
| 4,641,366 | A | 2/1987 | Yokoyama et al. | |
| 4,809,695 | A | 3/1989 | Gwathmey et al. | |
| 4,917,089 | A | 4/1990 | Sideris | |
| 4,994,077 | A | 2/1991 | Dobben | |
| 5,042,707 | A | 8/1991 | Taheri | |
| 5,049,153 | A | 9/1991 | Nakao et al. | |
| 5,069,679 | A | 12/1991 | Taheri | |
| 5,171,252 | A | 12/1992 | Friedland | |
| 5,209,756 | A | 5/1993 | Seedhom et al. | |
| 5,226,429 | A | 7/1993 | Kuzmak | |
| 5,226,911 | A | 7/1993 | Chee et al. | |
| 5,234,437 | A | 8/1993 | Sepetka | |
| 5,250,071 | A | 10/1993 | Palermo | |
| 5,254,130 | A | 10/1993 | Poncet et al. | |
| 5,261,916 | A | 11/1993 | Engelson | |
| 5,312,415 | A | 5/1994 | Palermo | |
| 5,332,402 | A | 7/1994 | Teitelbaum | |
| 5,350,397 | A | 9/1994 | Palermo et al. | |
| 5,383,886 | A | 1/1995 | Kensey et al. | |
| 5,403,326 | A | 4/1995 | Harrison et al. | |
| 5,411,552 | A | 5/1995 | Anderson et al. | |
| 5,417,700 | A | 5/1995 | Egan | |
| 5,423,858 | A | 6/1995 | Bolanos et al. | |
| 5,423,882 | A | 6/1995 | Jackman et al. | |
| 5,450,860 | A | 9/1995 | O'Connor | |
| 5,478,309 | A | 12/1995 | Sweezer et al. | |
| 5,478,353 | A | 12/1995 | Yoon | |
| 5,520,701 | A | 5/1996 | Lerch | |
| 5,522,873 | A | 6/1996 | Jackman et al. | |
| 5,536,251 | A | 7/1996 | Evard et al. | |
| 5,542,949 | A | 8/1996 | Yoon | |
| 5,554,185 | A | 9/1996 | Block et al. | |
| 5,571,137 | A | 11/1996 | Marlow et al. | |
| 5,571,215 | A | 11/1996 | Sterman et al. | |
| 5,618,306 | A | 4/1997 | Roth et al. | |
| 5,634,932 | A | 6/1997 | Schmidt | |
| 5,640,955 | A | 6/1997 | Ockuly et al. | |
| 5,690,671 | A | 11/1997 | McGurk et al. | |
| 5,695,504 | A | 12/1997 | Gifford, III et al. | |
| 5,713,910 | A | 2/1998 | Gordon et al. | |
| 5,716,367 | A | 2/1998 | Koike et al. | |
| 5,718,725 | A | 2/1998 | Sterman et al. | |
| 5,719,725 | A | 2/1998 | Nakao | |
| 5,741,280 | A | 4/1998 | Fleenor | |
| 5,769,812 | A | 6/1998 | Stevens et al. | |
| 5,797,927 | A | 8/1998 | Yoon | |
| 5,797,960 | A | 8/1998 | Stevens et al. | |
| 5,810,847 | A | 9/1998 | Laufer et al. | |
| 5,823,956 | A | 10/1998 | Roth et al. | |
| 5,824,065 | A | 10/1998 | Gross | |
| 5,827,237 | A | 10/1998 | Macoviak et al. | |
| 5,829,447 | A | 11/1998 | Stevens et al. | |
| 5,833,671 | A | 11/1998 | Macoviak et al. | |
| 5,836,955 | A | 11/1998 | Buelna et al. | |
| 5,840,081 | A | 11/1998 | Andersen et al. | |
| 5,855,614 | A | 1/1999 | Stevens et al. | |
| 5,879,307 | A | 3/1999 | Chio et al. | |
| 5,885,271 | A | 3/1999 | Hamilton et al. | |
| 5,916,147 | A | 6/1999 | Boury | |
| 5,928,224 | A | 7/1999 | Laufer | |
| 5,947,363 | A | 9/1999 | Bolduc et al. | |
| 5,954,732 | A | 9/1999 | Hart et al. | |
| 5,980,455 | A | 11/1999 | Daniel et al. | |
| 5,989,284 | A | 11/1999 | Laufer | |
| 6,019,722 | A | 2/2000 | Spence et al. | |
| 6,077,214 | A | 6/2000 | Mortier et al. | |
| 6,117,144 | A | 9/2000 | Nobles et al. | |
| 6,132,447 | A | 10/2000 | Dorsey | |
| 6,143,024 | A | 11/2000 | Campbell et al. | |
| 6,165,183 | A | 12/2000 | Kuehn et al. | |
| 6,190,408 | B1 | 2/2001 | Melvin | |
| 6,210,432 | B1 | 4/2001 | Solem et al. | |
| 6,269,819 | B1 * | 8/2001 | Oz et al. | 606/142 |
| 6,299,637 | B1 | 10/2001 | Shaolian et al. | |
| 6,306,133 | B1 | 10/2001 | Tu et al. | |
| 6,332,893 | B1 | 12/2001 | Mortier et al. | |
| 6,355,030 | B1 | 3/2002 | Aldrich et al. | |
| 6,402,781 | B1 | 6/2002 | Langberg et al. | |
| 6,406,420 | B1 | 6/2002 | McCarthy et al. | |
| 6,537,314 | B2 | 3/2003 | Langberg et al. | |
| 6,562,037 | B2 | 5/2003 | Paton et al. | |
| 6,575,971 | B2 | 6/2003 | Hauck et al. | |
| 6,585,761 | B2 | 7/2003 | Taheri | |
| 6,619,291 | B2 | 9/2003 | Hlavka et al. | |
| 6,626,899 | B2 | 9/2003 | Houser et al. | |
| 6,626,930 | B1 | 9/2003 | Allen et al. | |
| 6,656,221 | B2 | 12/2003 | Taylor et al. | |
| 6,689,164 | B1 | 2/2004 | Seguin | |
| 6,701,929 | B2 | 3/2004 | Hussein | |
| 6,702,826 | B2 | 3/2004 | Liddicoat et al. | |
| 6,709,382 | B1 | 3/2004 | Horner | |
| 6,709,456 | B2 | 3/2004 | Langberg et al. | |
| 6,723,038 | B1 | 4/2004 | Schroeder et al. | |
| 6,726,716 | B2 | 4/2004 | Marquez | |
| 6,740,107 | B2 | 5/2004 | Loeb et al. | |
| 6,746,471 | B2 | 6/2004 | Mortier et al. | |
| 6,755,777 | B2 | 6/2004 | Schweich et al. | |
| 6,764,510 | B2 | 7/2004 | Vidlund et al. | |
| 6,770,083 | B2 | 8/2004 | Seguin | |
| 6,797,001 | B2 | 9/2004 | Mathis et al. | |
| 6,797,002 | B2 | 9/2004 | Spence et al. | |
| 6,875,224 | B2 | 4/2005 | Grimes | |
| 6,945,978 | B1 | 9/2005 | Hyde | |
| 6,949,122 | B2 | 9/2005 | Adams et al. | |
| 7,011,669 | B2 | 3/2006 | Kimblad | |
| 7,112,207 | B2 | 9/2006 | Allen et al. | |
| 7,497,822 | B1 * | 3/2009 | Kugler et al. | 606/151 |
| 7,533,790 | B1 * | 5/2009 | Knodel et al. | 606/139 |
| 2002/0013571 | A1 | 1/2002 | Goldfarb et al. | |
| 2002/0035361 | A1 | 3/2002 | Houser et al. | |
| 2002/0087148 | A1 | 7/2002 | Brock et al. | |
| 2002/0087169 | A1 | 7/2002 | Brock et al. | |
| 2002/0156526 | A1 | 10/2002 | Hlavka et al. | |
| 2002/0161378 | A1 | 10/2002 | Downing | |
| 2002/0169360 | A1 | 11/2002 | Taylor et al. | |
| 2002/0183766 | A1 | 12/2002 | Seguin | |
| 2003/0050693 | A1 | 3/2003 | Quijano et al. | |
| 2003/0069570 | A1 | 4/2003 | Witzel et al. | |
| 2003/0069593 | A1 | 4/2003 | Tremulis et al. | |
| 2003/0069636 | A1 | 4/2003 | Solem et al. | |
| 2003/0074012 | A1 | 4/2003 | Nguyen et al. | |
| 2003/0078654 | A1 | 4/2003 | Taylor et al. | |
| 2003/0083742 | A1 | 5/2003 | Spence et al. | |
| 2003/0105519 | A1 | 6/2003 | Fasol et al. | |
| 2003/0120341 | A1 | 6/2003 | Shennib et al. | |
| 2003/0130730 | A1 | 7/2003 | Cohn et al. | |
| 2003/0167071 | A1 | 9/2003 | Martin et al. | |
| 2003/0187467 | A1 | 10/2003 | Schreck | |
| 2003/0229395 | A1 | 12/2003 | Cox | |
| 2003/0233038 | A1 | 12/2003 | Hassett | |
| 2004/0003819 | A1 | 1/2004 | St. Goar et al. | |
| 2004/0019377 | A1 | 1/2004 | Taylor et al. | |
| 2004/0019378 | A1 | 1/2004 | Hlavka et al. | |
| 2004/0024414 | A1 | 2/2004 | Downing | |
| 2004/0030382 | A1 | 2/2004 | St. Goar et al. | |
| 2004/0039442 | A1 | 2/2004 | St. Goar et al. | |
| 2004/0039443 | A1 | 2/2004 | Solem et al. | |
| 2004/0044350 | A1 | 3/2004 | Martin et al. | |
| 2004/0049211 | A1 | 3/2004 | Tremulis et al. | |
| 2004/0073302 | A1 | 4/2004 | Rourke et al. | |
| 2004/0088047 | A1 | 5/2004 | Spence et al. | |

| | | | |
|---|---|---|---|
| 2004/0097979 | A1 | 5/2004 | Svanidze et al. |
| 2004/0106989 | A1 | 6/2004 | Wilson et al. |
| 2004/0111099 | A1 | 6/2004 | Nguyen et al. |
| 2004/0122448 | A1 | 6/2004 | Levine |
| 2004/0127981 | A1 | 7/2004 | Rahdert et al. |
| 2004/0127982 | A1 | 7/2004 | Machold et al. |
| 2004/0127983 | A1 | 7/2004 | Mortier et al. |
| 2004/0133062 | A1 | 7/2004 | Pai et al. |
| 2004/0133063 | A1 | 7/2004 | McCarthy et al. |
| 2004/0133192 | A1 | 7/2004 | Houser et al. |
| 2004/0133220 | A1 | 7/2004 | Lashinski et al. |
| 2004/0133240 | A1 | 7/2004 | Adams et al. |
| 2004/0133273 | A1 | 7/2004 | Cox |
| 2004/0138744 | A1 | 7/2004 | Lashinski et al. |
| 2004/0138745 | A1 | 7/2004 | Macoviak et al. |
| 2004/0148021 | A1 | 7/2004 | Cartledge et al. |
| 2004/0152947 | A1 | 8/2004 | Schroeder et al. |
| 2004/0153144 | A1 | 8/2004 | Seguin |
| 2004/0158123 | A1 | 8/2004 | Jayaraman |
| 2004/0162610 | A1 | 8/2004 | Laiska et al. |
| 2004/0167539 | A1 | 8/2004 | Kuehn et al. |
| 2004/0193191 | A1 | 9/2004 | Starksen et al. |
| 2004/0215339 | A1 | 10/2004 | Drasler et al. |
| 2004/0220593 | A1 | 11/2004 | Greenhalgh |
| 2004/0220657 | A1 | 11/2004 | Nieminen et al. |
| 2004/0225300 | A1 | 11/2004 | Goldfarb et al. |
| 2004/0236354 | A1 | 11/2004 | Seguin |
| 2004/0243229 | A1 | 12/2004 | Vidlund et al. |
| 2004/0249452 | A1 | 12/2004 | Adams et al. |
| 2004/0249453 | A1 | 12/2004 | Cartledge et al. |
| 2005/0004583 | A1 | 1/2005 | Oz et al. |
| 2005/0004668 | A1 | 1/2005 | Aklog et al. |
| 2005/0021056 | A1 | 1/2005 | St. Goar et al. |
| 2005/0021057 | A1 | 1/2005 | St. Goar et al. |
| 2005/0033446 | A1 | 2/2005 | Deem et al. |
| 2005/0038508 | A1 | 2/2005 | Gabbay |
| 2005/0049698 | A1 | 3/2005 | Bolling et al. |
| 2005/0055089 | A1 | 3/2005 | Macoviak et al. |
| 2005/0059351 | A1 | 3/2005 | Cauwels et al. |
| 2005/0149014 | A1 | 7/2005 | Hauck et al. |
| 2005/0159810 | A1 | 7/2005 | Filsoufi |
| 2005/0197694 | A1 | 9/2005 | Pai et al. |
| 2005/0197695 | A1 | 9/2005 | Stacchino et al. |
| 2005/0216039 | A1 | 9/2005 | Lederman |
| 2005/0228422 | A1 | 10/2005 | Machold et al. |
| 2005/0228495 | A1 | 10/2005 | Macoviak |
| 2005/0251001 | A1 | 11/2005 | Hassett |
| 2005/0267493 | A1 | 12/2005 | Schreck et al. |
| 2005/0273160 | A1 | 12/2005 | Lashinski et al. |
| 2006/0058871 | A1 | 3/2006 | Zakay et al. |
| 2006/0195012 | A1 | 8/2006 | Mortier et al. |
| 2006/0252984 | A1 | 11/2006 | Rahdert et al. |

FOREIGN PATENT DOCUMENTS

| | | | |
|---|---|---|---|
| EP | 179562 | | 4/1986 |
| EP | 558031 | | 9/1993 |
| EP | 0684012 | A2 | 11/1995 |
| EP | 0684012 | A3 | 11/1995 |
| EP | 0684012 | B1 | 11/1995 |
| GB | 1598111 | | 9/1981 |
| GB | 2151142 | | 7/1985 |
| JP | 11089937 | | 4/1999 |
| WO | WO 81/00668 | | 3/1981 |
| WO | WO 91/01689 | | 2/1991 |
| WO | WO 91/18881 | | 12/1991 |
| WO | WO 92/12690 | | 8/1992 |
| WO | WO 94/18881 | | 9/1994 |
| WO | WO 94/18893 | | 9/1994 |
| WO | WO 97/39688 | | 10/1997 |
| WO | WO 98/07375 | | 2/1998 |
| WO | WO 98/30153 | | 7/1998 |
| WO | WO 98/35638 | | 8/1998 |
| WO | WO 99/00059 | | 1/1999 |
| WO | WO 99/01377 | | 1/1999 |
| WO | WO 99/07354 | | 2/1999 |
| WO | WO 00/03759 | | 1/2000 |
| WO | WO 00/59382 | A1 | 10/2000 |
| WO | WO 00/60995 | | 10/2000 |
| WO | WO 01/26557 | | 4/2001 |
| WO | WO 01/26586 | | 4/2001 |
| WO | WO 01/28432 | | 4/2001 |
| WO | WO 01/54618 | | 8/2001 |
| WO | WO 02/03892 | | 1/2002 |
| WO | WO 03/001893 | | 1/2003 |
| WO | WO 03/020179 | | 3/2003 |
| WO | WO 03/028558 | | 4/2003 |
| WO | WO 03/037171 | | 5/2003 |
| WO | WO 03/047467 | | 6/2003 |
| WO | WO 03/049619 | | 6/2003 |
| WO | WO 03/073910 | | 9/2003 |
| WO | WO 03/073913 | | 9/2003 |
| WO | WO 03/105667 | A3 | 12/2003 |
| WO | WO 2004/004607 | | 1/2004 |
| WO | WO 2004/012583 | | 2/2004 |
| WO | WO 2004/019811 | | 3/2004 |
| WO | WO 2004/082538 | A2 | 3/2004 |
| WO | WO 2004/030570 | | 4/2004 |
| WO | WO 2004/037317 | | 5/2004 |
| WO | WO 2004/045370 | | 6/2004 |
| WO | WO 2004/045378 | A2 | 6/2004 |
| WO | WO 2004/045463 | | 6/2004 |
| WO | WO 2004/047679 | | 6/2004 |
| WO | WO 2004/062725 | | 7/2004 |
| WO | WO 2004/082523 | A2 | 9/2004 |
| WO | WO 2004/093730 | | 11/2004 |
| WO | WO 2004/112585 | | 12/2004 |
| WO | WO 2004/112651 | | 12/2004 |
| WO | WO 2005/002424 | | 1/2005 |
| WO | WO 2005/018507 | | 3/2005 |
| WO | WO 2005/027797 | A1 | 3/2005 |
| WO | WO 2005/032421 | A2 | 4/2005 |
| WO | WO 2005/062931 | A2 | 7/2005 |
| WO | WO 2005/112792 | | 12/2005 |
| WO | WO 2006/105008 | | 10/2006 |
| WO | WO 2006/105009 | | 10/2006 |
| WO | WO 2006/115875 | | 11/2006 |
| WO | WO 2006/115876 | | 11/2006 |

OTHER PUBLICATIONS

Abe et al., "Updated: De Vega's Annuloplasty for Acquired Tricuspid Disease: Early and late results in 110 Patients" *Ann. Thorac. Surg.* (1996) 62: 1876-1877.

Alvarez et al., "Repairing the Degenerative Mitral Valve: Ten- to Fifteen-Year Follow-Up" *J. Thoracic. Cardiovasc. Surg.* (1996) 112:238-247.

Bach et al., "Early Improvement in Congestive Heart Failure After Correction of Secondary Mitral Regurgitation in End-Stage Cardiomyopathy" *Am. Heart J.* (1995) 129:1165-1170.

Bach et al., "Improvement Following Correction Of Secondary Mitral Regurgitation In End-Stage Cardiomyopathy With Mitral Annuloplasty" *Am. J. Cardiol.* (1996) 78:966-969.

Bailey, *Surgery of the Heart*, Chapter 20, 1995, pp. 686-737.

Bolling et al., "Surgery For Acquired Heart Disease: Early Outcome Of Mitral Valve Reconstruction In Patients With End-Stage Cardiomyopathy", *J. Thoracic. Cardiovasc, Surg.*, (Apr. 1995), 109(4): 676-683.

Dec et al., "Idiopathic Dilated Cardiomyopathy" *N. Engl. J. Med.* (1994) 331:1564-1575.

Fucci et al., "Improved Results with Mitral Valve Repair Using New Surgical Techniques" Eur. *J. Cardiothorac. Surg.* (1995) 9:621-627 (Medline Record enclosed herewith).

Kameda et al., "Annuloplasty for Severe Mitral Regurgitation to Dilated Cardiomyopathy" *Am. Thorac. Surg.* (1996) 61:1829-1832.

Khan et al., "Biade Atrial Septostomy: Experience with First 50 Procedures" *Cathet. Cardiovasc. Diagn.* (1991) 23:257-262.
Maisano et al., "The Edge-to-Edge Technique: A Simplified Method to Correct Mitral Insufficiency" *Eur. J. Cardiothorac. Surg.* (1998) 13:240-246.
McCarthy et al., "Tricuspid Valve Repair with the Cosgrove-Edwards Annuloplasty System" *Am. Thorac. Surg.* (1997) 64:267-268.
Park et al., "Clinical Use of a Blade Atrial Septostomy" *Circulation* (1978) 58:600-608.
Reul et al., "Mitral Valve Reconstruction for Mitral Insufficiency," *Progress in Cardiovascular Diseases*, No. 6, May/Jun. 1997, pp. 567-599, vol. XXXIX.
Ricchi et al., "Linear Segmental Annuloplasty for Mitral Valve Repair" *Ann. Thorac. Surg.* (1997) 63:1805-1806.
Tager et al., "Long-Term Follow-Up of Rheumatic Patients Undergoing Left-Sided Valve Replacement with Tricuspid Annuloplasty -Validityof Preoperative Echocardiographic Criteria in the Decision to Perform Tricuspid Annuloplasty" *Am. J. Cardiol.* (1998) 81:1013-1016.
Uchida et al., "Percutaneous Cardiomyotomy and Valvultomy with Angioscopic Guidance" *Am. Heart J.* (1991) 121:1221-1224.
Umana et al., "Bow-tie Mitral Valve Repair Successfully Addresses Subvalvular Dysfunction in Ischemic Mitral Regurgitation" (1997) *Surgical Forum* pp. 279-280.
Umana et al., "Bow-tie mitral valve repair: An adjuvant technique for ischemic mitral regurgitation" *Ann. Thorac. Surg.* (1998) 66:1640-1646.
Bernal et al., "The 'Valve Racket': a new and different concept of atrioventricular valve repair," Eur. J. Cardio-thoracic Surgery 29:1026-29 (2006).
Derwent citing German language patent EP 684012 published Nov. 12, 1995 for: "Thread for constructing surgical seam has flexible section with two ends, with lower fastening part on thread first end having hollow cylinder with continuous hole through which surgical needle threads" 2 pgs.
Derwent citing Japanese language patent JP 11089937 published Jun. 4, 1999 for: "Catheter for mitral regurgitation test—includes jet nozzles provided on rear side of large diametered spindle shaped portion attached to end of narrow diametered tube" 1 pg.
Filsoufi et al., "Restoring Optimal Surface of Coaptation With a Mini Leaflet Prosthesis: A New Surgical Concept for the Correction of Mitral Valve Prolapse," Int'l. Soc. for Minimally Invasive Cardiothoracic Surgery 1(4):186-87 (2006).
Langer et al., "Posterior mitral leaflet extensions. An adjunctive repair option for ischemic mitral regurgitation?," J. Thorac. Cardiovasc. Surf. 131:868-77 (2006).

* cited by examiner

SURGICAL DEVICE FOR CONNECTING SOFT TISSUE

CROSS-REFERENCES TO RELATED APPLICATIONS

This application is a continuation of U.S. patent application Ser. No. 10/877,279, filed on Jun. 24, 2004, which was a divisional of U.S. patent application Ser. No. 10/202,599, filed Jul. 24, 2002, now U.S. Pat. No. 6,770,083, which was a divisional of U.S. patent application Ser. No. 09/523,018, filed Mar. 10, 2000, now U.S. Pat. No. 6,461,366, which was a continuation of PCT/FR98/01960, which designated the United States, filed Sep. 12, 1997, the full disclosure of which is incorporated herein by reference.

BACKGROUND OF THE INVENTION

This invention provides a surgical device allowing the percutaneous connection of two soft tissue areas that are ordinarily separate. This device is particularly intended for reconstruction of heart valves, especially the mitral valve, and for the treatment of any malformation of a heart septum.

In a condition known as mitral insufficiency, the mitral valve does not completely shut, and does not prevent the back-flow of blood to the left atrium from the left ventricle. Surgical repair is then necessary. In a current procedure, a sternotomy is performed. The patient is then placed under extra-corporal blood circulation while the heart is stopped, and the heart chambers are opened to gain access to the mitral valve, usually through the left atrium. Once the mitral valve is accessed, repair procedures include annuloplasty and, more recently, suturing of the free edge of the anterior leaflet to the free edge of the back leaflet where the mitral insufficiency occurs.

These procedures are complicated and require general anesthesia, sternotomy and extra-corporal blood circulation. They also require high doses of anti-coagulant therapy adding to the operative risk of a myocardial infarction and hemorrhage.

SUMMARY OF THE INVENTION

The methods of the present invention are performed percutaneously, diminishing considerably these risks. A surgical device allows the connection of two zones of soft tissue that are usually separate. In a particular embodiment, a connection is formed between a free edge area of an anterior mitral leaflet and a free edge area of a back mitral leaflet. Suitable surgical devices for performing tissue connection are described for example in EP 558 031 and WO 94/18893, and may comprise:

(a) a tube which may be inserted percutaneously until its distal extremity reaches the area around the tissues to be connected; and (b) two elongated elements inside that tube, each of which comprises a distal extremity having a device that grasps one of the two tissues to be connected;

(c) wherein the distal extremities of these elongated elements may be opened and closed in order to permit introduction into the desired area, allow the procedure.

Particular devices according to the present invention may further comprise:

(a) a grasping element, optionally having two parts for capturing each of the tissues to be connected, wherein the grasping or hooking element effects the connection of the two zones of tissue when brought close thereto by shifting of the portions of distal extremities to a position where they meet;

(b) a rod connected to each of the grasping or hooking elements and operated from the proximal end of the tube in order to axially shift the elongated element, wherein the rod can be separated from the grasping or hooking element upon pulling beyond a given threshold; and (c) a wedge inside the tube, allowing the axial immobilization of each grasping or hooking element while pulling on them.

The rod positions the insertion of the hooking element up to the level of the tissue edges to be connected. The rod also engages the hooking element against the wedge in order to open the two hooking parts.

According to the present invention, the device may be used to remotely grasp through a percutaneous passage, to draw together, and to connect the two zones of tissue by a simple external manipulation.

Preferably, the tube, the elongated elements, and the rod are flexible enough to be inserted percutaneously and through a patient's vasculature for the treatment of the leaflets of a cardiac valve, in particular the mitral valve. Each of the elongated elements is made out of an elastically flexible material, and one of these elongated elements diverges from the longitudinal axis of the other. The two elongated elements can move axially in relation to the tube between (a) a retracted position within the tube where the ends of the elongated elements are flexibly bent and closed together, and (b) a position where the ends of the elongated elements spring open and diverge from each other in a way that permits those ends to capture the soft tissues in order to grasp them.

The elongated elements may be deployed to allow their distal extremities to grasp the tissue areas or may be retracted in order to make the insertion, shifting or removal of the apparatus easier. Each elongated element may comprise a rod made of elastic material, with a curved distal extremity and/or a harpoon shape, and a sheath able to slide axially in a forward position to cover the distal extremity and slide back to uncover it.

According to a variation, each elongated element can be composed of a tube linked to a system that contracts its internal volume in order to grasp the corresponding tissue area, and expands to release the tissue with no lesion. In this case, the wide-mouthed shape of the elongated element's distal extremity will insure a large enough grasping surface.

Preferably, the device includes two hooking elements. One is operated on the distal side of the tissues, and the other, to be operated on the proximal side of the tissues, is situated between the first hooking element and the wedge element. This way the two hooking elements can be operated on both sides of the tissues and can be pressed together for a perfect attachment of those tissues.

BRIEF DESCRIPTION OF THE DRAWINGS

For greater clarity, the invention is described again in reference to the enclosed Figures representing two unrestricted examples of the invention in its optimal capacity.

DESCRIPTION OF THE SPECIFIC EMBODIMENTS

Figure 1:
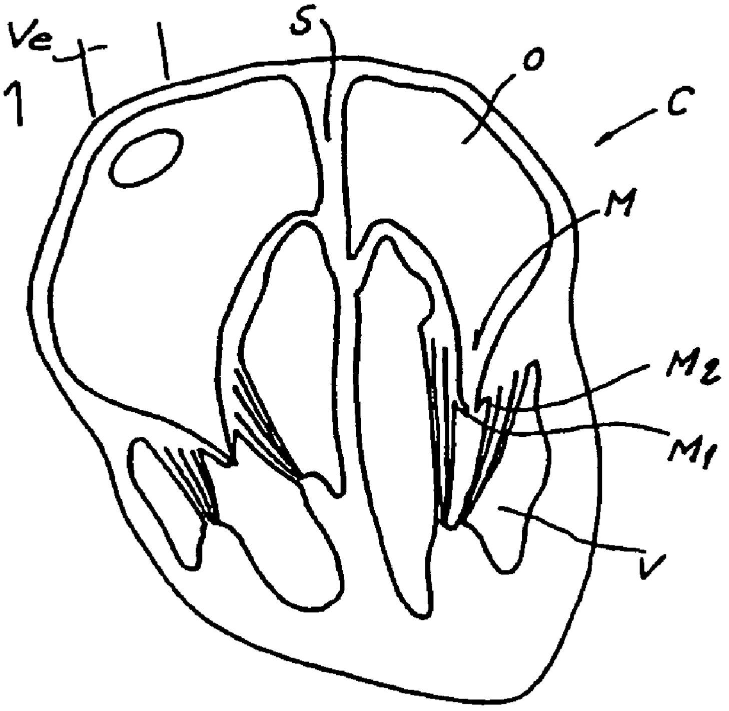
FIG. 1 shows a longitudinal section of a heart with a mitral valve that does not shut properly and has to be treated with this device.
Figure 2:
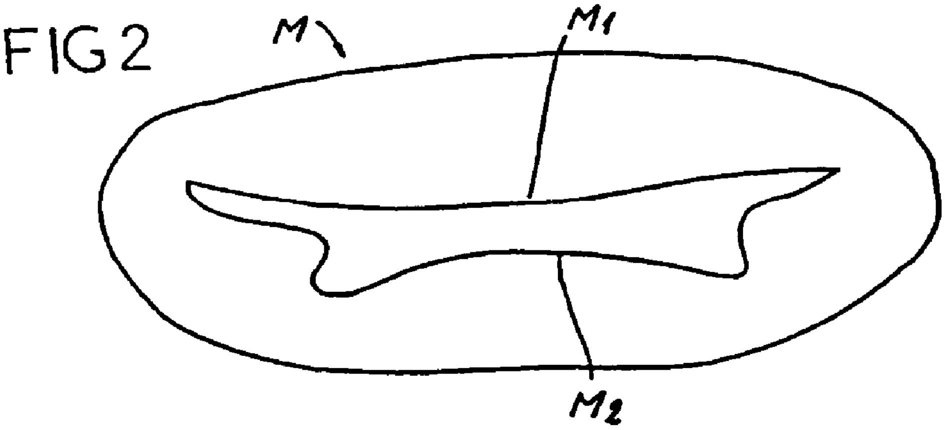
FIG. 2 shows the mitral valve before treatment.
Figure 3:
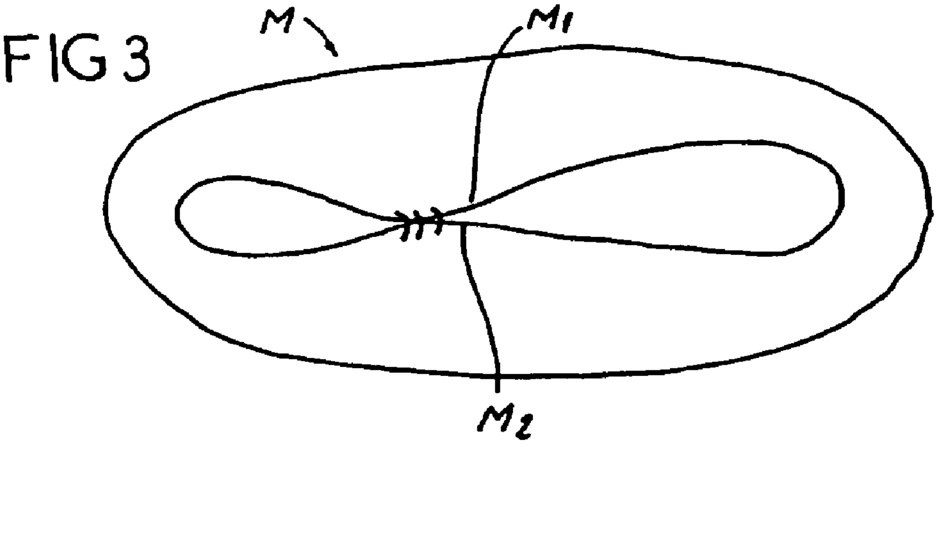
FIG. 3 shows a mitral valve similar to FIG. 2 after treatment by suture according to the usual procedure.

FIG. 1 shows a heart C with a mitral valve M having poorly opposed leaflets (M1, M2). Thus, the valve M does not shut tightly and no longer performs its back-flow function between the left atrium O and the left ventricle V. According to conventional procedures, after sternotomy, the patient is placed under extra-corporal blood circulation. The heart is stopped and the heart chambers are opened to directly reach to the valve M and stitch together the free opposite edges of both leaflets (M1, M2) as shown on FIGS. 2 and 3. Connecting leaflets M1 to M2 restores a good attachment between them and restores the imperviousness of valve M.

Figure 4:
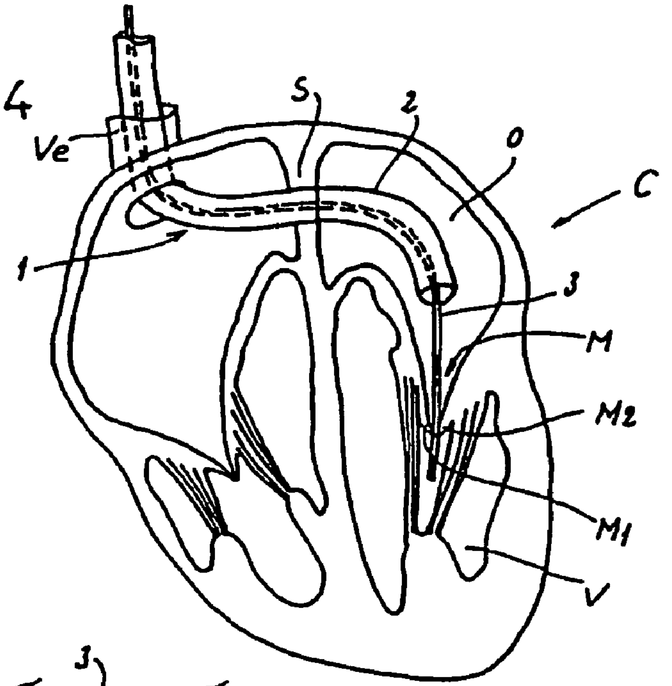
FIG. 4 is a view similar to that of FIG. 1, with the device of the present invention inserted into a heart.
Figure 5:
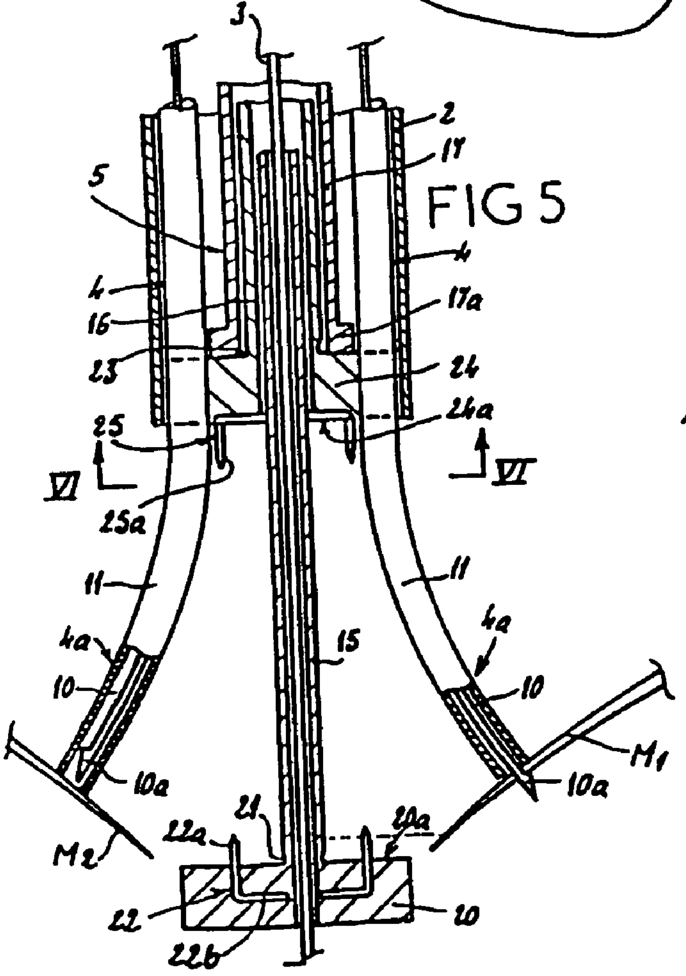
FIG. 5 is an enlarged view of a longitudinal section of the distal extremity of the device.

FIGS. 4 to 5 show a device (1) according to the present invention which enables the percutaneous connection of leaflet M1 to leaflet M2. This device (1) comprises an external tube (2), guidewire (3), two elongated elements (4), and a clipping system (5). The apparatus is sufficiently flexible to be percutaneously inserted into the heart C, through the patient's vascular, e.g., the Vena Cava Ve and the intra-atrial septum S. Guidewire (3) is inserted through valve M and so the distal extremity of external tube (2) is located in the left atrium O, with its distal opening facing mitral valve M.

Figure 7:
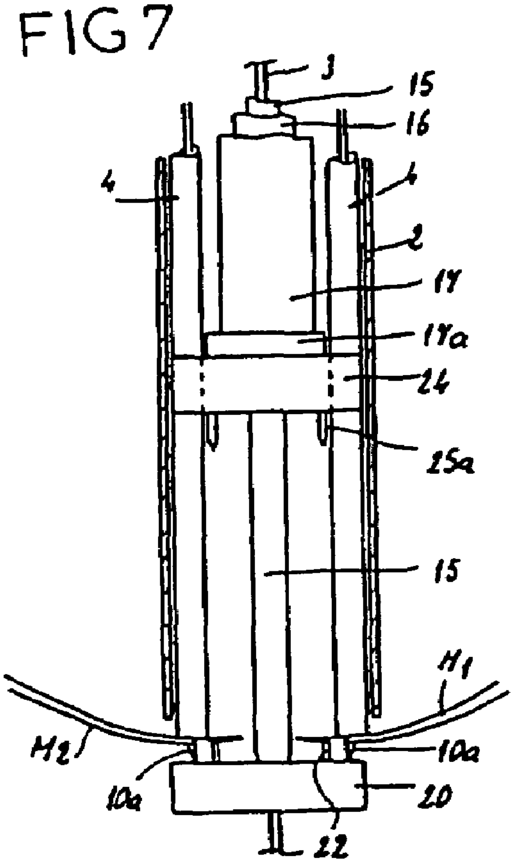
FIG. 7 and FIG. 8 are similar views to FIG. 5 at different stages of the procedure.
Figure 8:
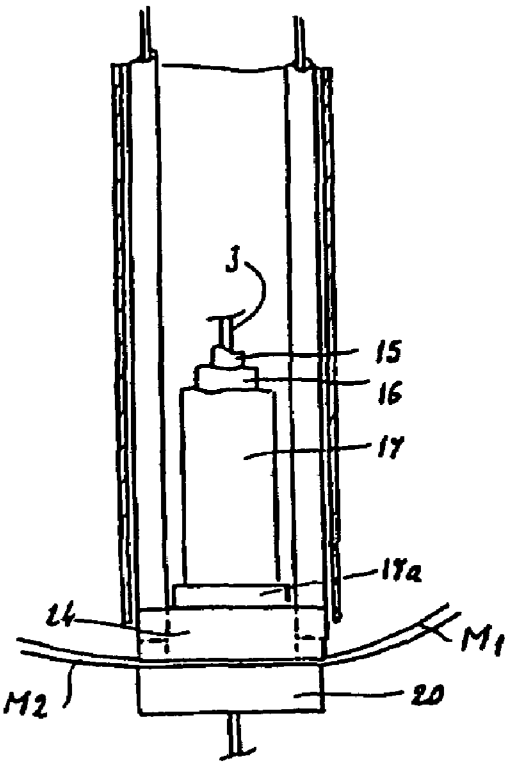

Each of the elongated elements (4) has a distal extremity (4*a*) that is normally curved to diverge outwardly. A rod (10) is made out of a relatively rigid but still elastic material, more particularly in metal, with a sheath (11) of synthetic material. The distal extremity (10*a*) of the rod (10) is sharp and more or less harpoon-shaped. The sheath (11) fits on the rod (10) and can slide axially to a forward position (as shown on left side of FIG. 5) in order to cover the distal extremity of the rod, and can slide back (as shown on the right side of FIG. 5) in order to uncover that same distal extremity (10*a*). The elongated elements (4) extend from the end of the tube (2). Because of this, they can be shifted axially in relation to the tube (2) between a retracted position where the extremities (10*a*) close together (FIGS. 7 and 8) and an extended position where these same extremities (10*a*) diverge from each other (FIG. 5). The clipping system (5) comprises three concentric tubular rods (15, 16, 17) that can be slidably introduced over the guidewire (3). Each rod can also slide axially in relation to the others. The internal rod (15) is linked to a disk (20) through a frangible area (21). The rod and disk (15 and 20) are made of molded synthetic material. The disk (20) is axially pierced in order to let the guidewire (3) pass through, and carries a clip (22). Side prongs (22*a*) of that clip extend from the proximal face (20*a*) of the disk (20). A central portion (22*b*) of the clip (22) having a central ring for receiving the guidewire (3) is embedded into the material of the disk (24).

Figure 6:
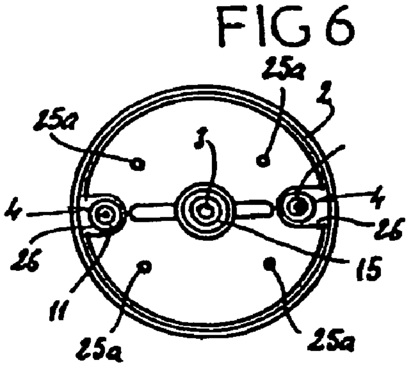
FIG. 6 shows a view of this distal extremity according to the line VI-VI of FIG. 5.

The intermediate rod (16) is also connected by a frangible area (23) to a disk (24) with two clips (25). Side prongs (25*a*) of these clips extend from the distal face (24*a*) of this disk (24), and central portions of the prongs are embedded into the material of the disk (24). On each side, the disk (24) has two diametrically opposed notches (26, FIG. 6) to allow the passage of the elongated elements (4). The external rod (17) has an expanded distal extremity (17*a*) which engages the proximal face of the disk (24). Each of these rods (15, 16, 17) can be extended beyond the proximal extremity of tube (2) so they can be shifted by the operator.

A handle or other structure for manipulating the rods (15, 16, 17) will usually be provided at a proximal end of the device. The handle will permit deployment rod (15) while rod (17) is held in a desired position in relation to tube (2), and then deployment rod (16), while rod (17) is also held in the desired position in relation to tube (2).

In practice, under X-ray or echography control, the guidewire (3) is first inserted through Vena Cava Ve, the intra-atrial septum S, and mitral valve M. Then tube (2) and its internal parts are inserted into the Vena Cava Ve and through the septum S until the distal extremity of tube (2) is directed at mitral valve M (FIG. 4). At this stage, disk (20) should be held at the opening of tube 2 (FIG. 5), while elongate elements (4) are retracted so that their distal extremities are retracted into slots (26).

When the distal extremity of tube (2) is in the proper position, rod (15) is shifted to advance disk (20) beyond leaflets M1 and M2 and into the left ventricle V. Elongate elements (4) are then advanced to their extended positions, as shown in FIG. 5. As the elongate elements (4) are advanced, their distal extremities diverge. After the elements (4) are advanced, distal extremities (10*a*) of rods (10) are positioned close to leaflets (M1, M2). The sheaths (11) of elements (4) are then retracted in relation to the rods (10) in order to uncover the extremities (10*a*), each of which can then pierce and capture the adjacent leaflet M1 or M2. Tube (2) is then advanced over the elongate elements (4), drawing the distal extremities (4*a*) closer, as shown on FIG. 7. This action draws the free edges of leaflets M1 and M2 together.

Figure 9:
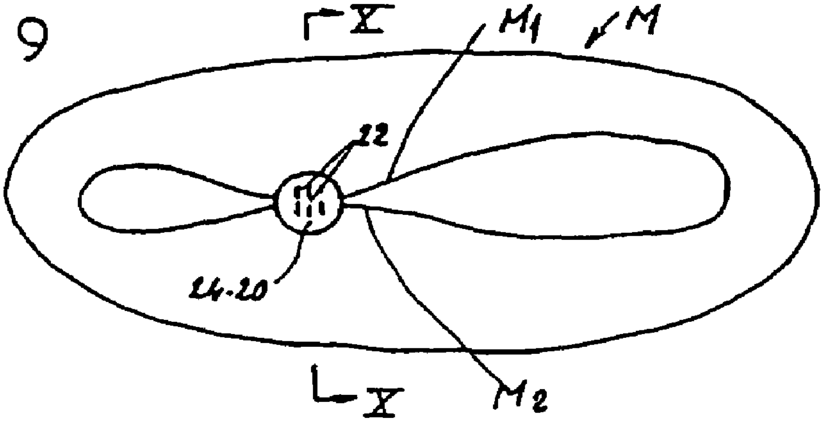
FIG. 9 is a similar view to FIG. 2 of the mitral valve after treatment with the device.
Figure 10:
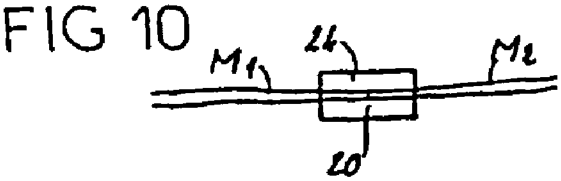
FIG. 10 is a view of this valve according to line X-X of FIG. 9.

Rod (17) is advanced distally in relation to tube (2), and rod (15) is pulled proximally in relation to tube (2) in order to insert the prongs (22*a* and 25*a*) of clips (22 and 25) into the leaflets M1 and M2. The tension on rod (15) forces the prongs (22*a* and 25*a*) against the opposed walls (20*a*, 24*a*) of the disks (20, 24) and breaks frangible area (21). This break gives the prongs of the clips enough freedom of movement to ensure a good connection between leaflets M1 and M2. The sheaths (11) are then advanced distally in relation to the rods (10) to engage leaflets (M1, M2). This facilitates the extremities (10*a*) of the rods from the leaflets (M1, M2). Rod (16) is then pulled while holding rod (17) in position to break frangible area (25). Leaflets (M1, M2) have thus been clipped to each other by their free edges, as shown in FIGS. 9 and 10.

Figure 11:
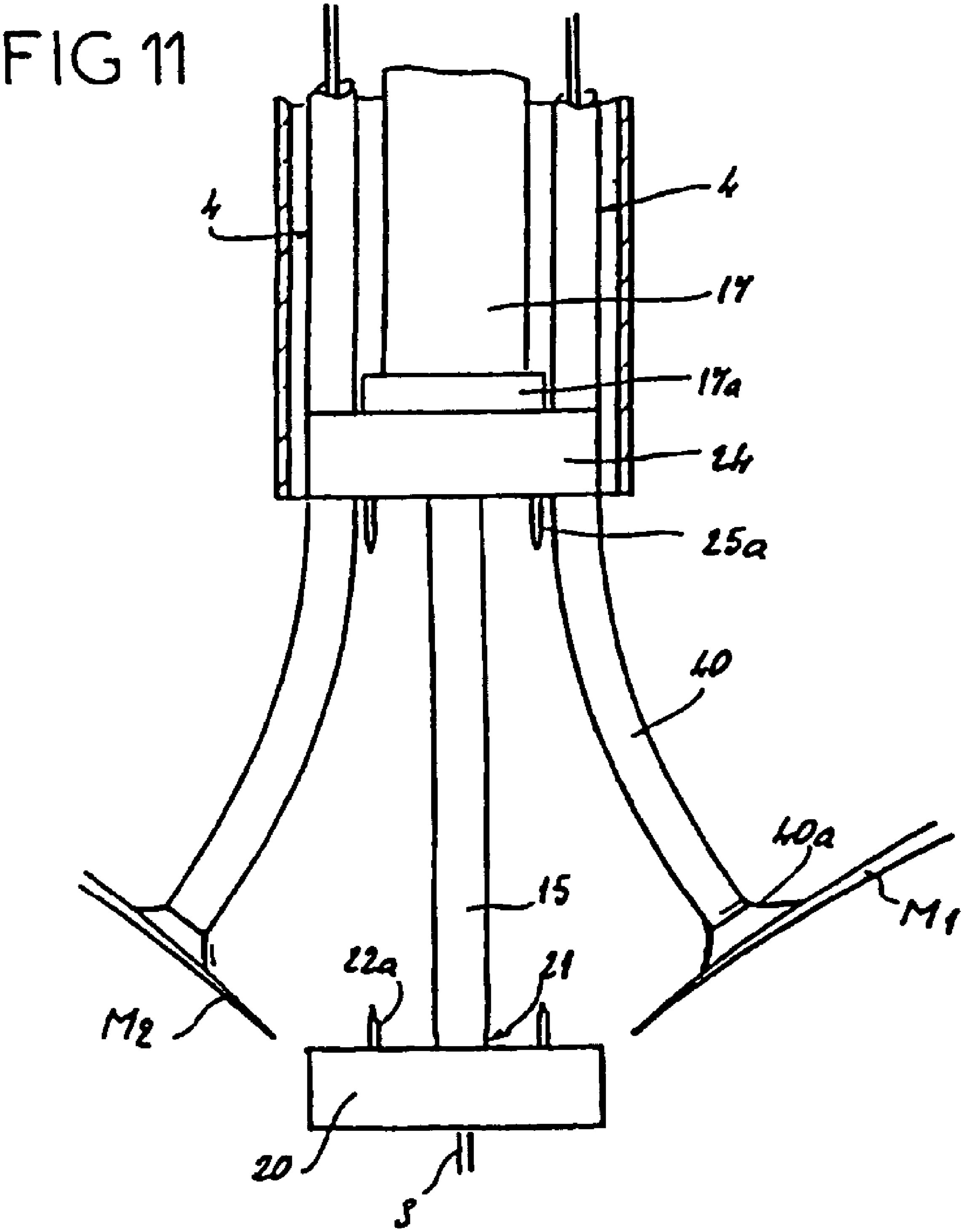
FIG. 11 illustrates an alternative embodiment of the device of the present invention.

FIG. 11 shows a variation of the apparatus where rods (10) and sheaths (11) have been replaced by two catheters (40) having trumpeted distal extremities (40*a*). These catheters (40) project beyond the proximal end of tube (2) and may be attached to syringes that permit the creation of negative pressure. The grasping or releasing of leaflets (M1, M2) is then achieved by controlling the internal pressure within catheters (40). The trumpeted ends (40*a*) ensure a sufficient grip on leaflets (M1, M2). Those ends (40*a*) are preferably sufficiently flexible enough to bend slightly when they are drawn between the wall of tube (2) and two lateral slots (26) of disk (20). The other parts of this alternative device are the same as already described and bear the same record numbers.

It goes without saying that the invention is not limited to the above example and is opened to different variations. For instance, the unstressed shape of the extremities (10*a*) that hook the tissues could be of a curved J which is straightened when drawn into the sheaths (11). The elongated parts (4) and the connecting system could also be placed in separate tubes. The device (1) could be inserted arterially as well as veinously.

What is claimed is:

1. A heart valve leaf fastener consisting of a first pair of arms and a second pair of arms, each pair having a suitable size for fastening heart valve leaflets and said two pairs of arms capable of fastening two adjacent leaflets, wherein the first pair of arms is adapted to be brought up beneath a pair of valve leaflets from the ventricular side and the second pair of arms is adapted to be brought down over the pair of valve leaflets from the atrial side to capture the leaflets therebetween, wherein the pairs of arms may be left to attach free ends of the leaflets together.

2. A heart valve leaflet fastener as in claim 1, further comprising at least one central core wherein said arms project from said core.

3. A heart valve leaflet fastener as in claim 1, wherein said arms pierce the leaflets.

4. A heart valve leaf fastener as in claim 1, further comprising two pairs of prongs, each prong having a size suitable for fastening heart valve leaflets.

5. A heart valve leaf fastener as in claim 4, wherein each pair of prongs projects from a disk.

6. A heart valve leaf fastener as in claim 5, wherein the pairs of prongs engage and penetrate the atrial and ventricular sides of the valve leaflets respectively as the disks are brought together.

7. A device for the treatment of cardiac valve insufficiency comprising:

a tube suitable for insertion through a patient's vasculature and into a chamber of a heart;

a pair of elongate elements for individually grasping at least two valve leaflets each valve leaflet having a free edge; and a connecting system for connecting the free edges of the at least two valve leaflets, wherein the connecting system comprises a clipping system consisting of a first pair of arms adapted to be brought up beneath the at least two valve leaflets from the ventricular side of each of the at least two valve leaflets and a second pair of arms adapted to be brought down over the at least two valve leaflets from the atrial side and wherein the first and second arms may be left to connect the free edges of the at least two valve leaflets.

8. The device of claim 7, further comprising a second tube for insertion through a patient's vasculature and into a chamber of a heart wherein the elongate elements are within the second tube.

9. The device of claim 7, further comprising a third tube for insertion through a patient's vasculature wherein the connecting system is within the third tube.

10. The device of claim 7, wherein the elongate elements are adapted for connection to a vacuum for grasping the at least two valve leaflets.

* * * * *